(12) United States Patent
Taden et al.

(10) Patent No.: US 7,973,158 B2
(45) Date of Patent: Jul. 5, 2011

(54) METHOD OF PREPARING BENZOXAZINES

(75) Inventors: Andreas J. Taden, Duesseldorf (DE); Puwei Liu, San Marcos, CA (US); Alex C. Wong, Pittsburg, CA (US); Eric A. Parker, Pleasant Hill, CA (US)

(73) Assignees: Henkel Corporation, Rocky Hill, CT (US); Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 12/434,081

(22) Filed: May 1, 2009

(65) Prior Publication Data

US 2009/0270615 A1  Oct. 29, 2009

Related U.S. Application Data

(63) Continuation of application No. PCT/US2007/024519, filed on Nov. 28, 2007.

(60) Provisional application No. 60/867,677, filed on Nov. 29, 2006.

(51) Int. Cl.
*C07D 265/12* (2006.01)

(52) U.S. Cl. ............................................ 544/90; 544/73

(58) Field of Classification Search .................... 544/90
See application file for complete search history.

(56) References Cited

U.S. PATENT DOCUMENTS

| | | | |
|---|---|---|---|
| 5,543,516 | A | 8/1996 | Ishida |
| 2003/0018131 | A1 | 1/2003 | Davis et al. |
| 2004/0068084 | A1 | 4/2004 | Hwang et al. |
| 2005/0042961 | A1 | 2/2005 | Lehmann et al. |

FOREIGN PATENT DOCUMENTS

| | | |
|---|---|---|
| CN | 1451679 | 10/2003 |
| EP | 1380607 | 1/2004 |
| JP | 102003082117 | 3/2003 |
| JP | 2005-213301 | 8/2005 |
| WO | WO 03/042196 | 5/2003 |
| WO | WO 2005/000955 | 1/2005 |
| WO | WO 2005/019291 | 3/2005 |

OTHER PUBLICATIONS

Burke et al. Journal of Organic Chemistry (1964), 29(4), 909-12.*

* cited by examiner

*Primary Examiner* — Kahsay T Habte
(74) *Attorney, Agent, or Firm* — Steven C. Bauman

(57) ABSTRACT

This invention relates to a novel synthesis for the preparation of benzoxazine components from phenolic components, aldehyde components, and amine components in a solvent other than toluene.

11 Claims, 3 Drawing Sheets

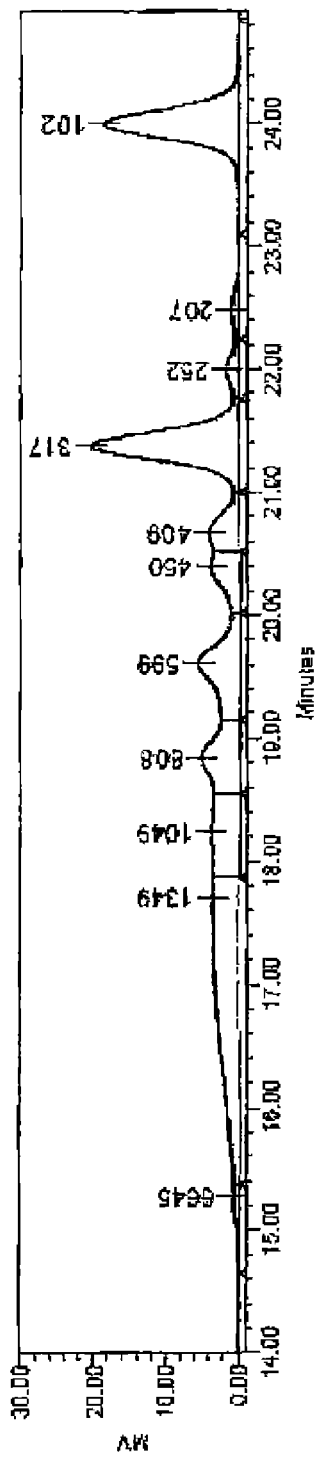
FIG. 2A TOLUENE PROCESS
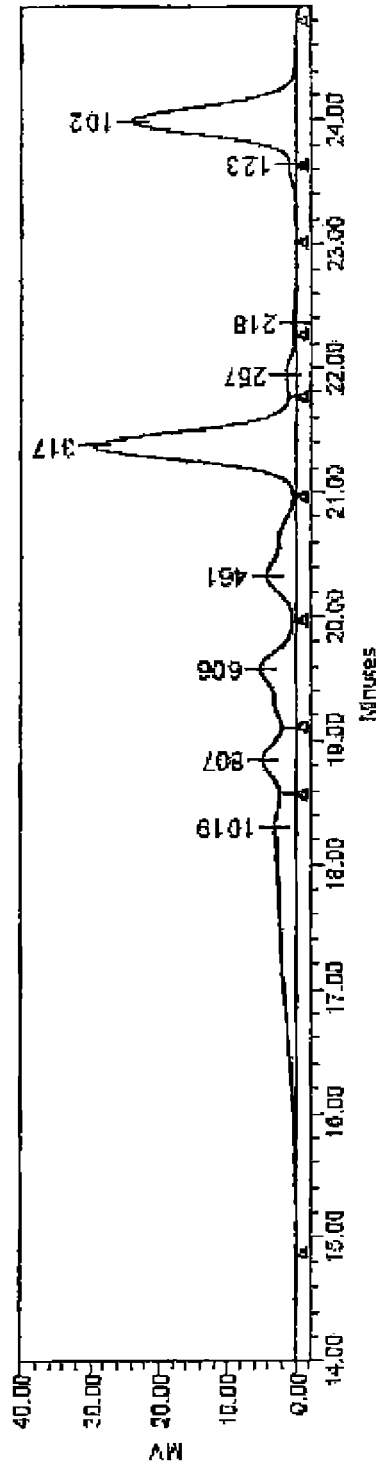
FIG. 2B ETHYL ACETATE PROCESS

METHOD OF PREPARING BENZOXAZINES

BACKGROUND OF THE INVENTION

1. Field of the Invention

This invention relates to a novel synthesis for the preparation of benzoxazine compounds from phenolic compounds, aldehyde compounds, and amine compounds.

2. Brief Description of Related Technology

Benzoxazines are ordinarily prepared by reacting a phenolic compound, with an aldehyde and an alkyl amine. This reaction is known to be conducted under solventless conditions or in a solvent, such as toluene, dioxane, alcohol or diethyl ether.

For instance, in U.S. Pat. No. 5,543,516 (Ishida) a method for preparing a benzoxazine compound is provided, in which a reaction mixture containing a phenolic compound, a primary amine, and an aldehyde is prepared without a separate solvent; the reactants are brought to a temperature at which the reactants combine chemically and are maintained at that temperature to reportedly form the benzoxazine compound.

And Chinese Patent Publication No. CN 1451679 (Cu) is directed to modified benzoxazine resins for RTM applications, and explains that in the past benzoxazine resins had been synthesized using organic solvents, such as toluene, dioxane and dimethyl benzene (citing to Chinese Patent Application No. ZL 94111852.5). In the CN '679 publication, however, toluene is used as the solvent in the working examples.

Benzoxazines are presently available from several sources commercially, including Huntsman Specialty Chemicals, Brewster, N.Y.; Georgia-Pacific Resins, Inc. and Shikoku Chemicals Corporation, Chiba, Japan, the last of which offers among others B-a, B-m, F-a, C-a and F-a benzoxazine resins. It is believed that these commercially available benzoxazines are prepared using toluene as a solvent.

However, these known synthetic methods and some commercial benzoxazines have shortcomings. For instance, some of the solvents used in the synthesis are toxic and thus desirably are avoided in the workplace, while others are removable at elevated temperature conditions that cause a premature degradation and/or polymerization of some benzoxazine compounds, resulting in compromised performance of curable compositions formulated with such benzoxazines.

The known synthetic method usually takes a relatively long period of time, i.e., at least several hours, to carry out the desired reaction, and to separate the reaction products. Purification of the end product oftentimes requires additional time. In addition, although the yield of benzoxazines is in many cases satisfactory, as noted many common solvents pose toxicity risks, which in many cases require expensive measures to eliminate, for instance the installation of costly solvent recovery systems.

There therefore exists a need for a synthetic method that overcomes these shortcomings.

SUMMARY OF THE INVENTION

The present invention provides a solution to the synthetic shortcomings described above.

More specifically, the present invention provides a method for preparing benzoxazine. The inventive method includes the steps of preparing a reaction mixture containing as reactants a phenolic compound, a primary amine compound, and an aldehyde compound in an alkyl ester solvent; and bringing the reactants to a temperature at which the reactants combine chemically and maintaining them at that temperature for a time sufficient to form the benzoxazine.

The benzoxazine synthesis using toluene as a solvent, for instance, suffers from the high boiling point of toluene, even under vacuum. As a result, high temperature is needed to remove the toluene solvent from the benzoxazine product. However, since the benzoxazine product is volatile to a certain extent under these high temperature conditions, the toluene solvent cannot be completely separated from the benzoxazine product without removing the benzoxazine product as well, and significantly advancing the benzoxazine product and thus reducing its shelf life stability. Reference to FIGS. 1 and 2 show that the benzoxazine product synthesized in a toluene solvent still contains residual toluene as indicated by GC and shows instability at 120° C. by rheometrics.

With this as background, an alternative solvent was desirable, whose properties include water immiscibility; readily solubilizes raw materials, any intermediate products that form, and the benzoxazine product; a boiling point between 65° C. to 105° C. under ambient pressure; and low toxicity. The solvent of choice, as described in more detail below, is an alkyl ester, such as ethyl acetate. Ethyl acetate has a boiling point of 76.5-77.5° C. at ambient pressure. Propyl acetate (whose boiling point is 102° C.) and isopropyl acetate (whose boiling point is 85-91° C.) may be used as well. Likewise, while not an acetate, propyl formate (whose boiling point is 80-81° C.) may be used as well and is thus embraced by an alkyl ester.

The following solvent families have been determined to be unsuitable for the commercial synthesis of benzoxazines for the reasons given:

Aromatics (such as benzene, toluene or xylene) either because of their toxicity or too high a boiling point, or both, are not suited for the practice of the present invention.

Alcohols (such as methanol, ethanol, or t-butyl alcohol), either because of their miscibility with water or too high a boiling point, or both, are not suited for the practice of the present invention.

Ethers (such as ethyl ether, dipropyl ether or THF), because of their toxicity, are not suited for the practice of the present invention.

Ketones (such as acetone or MEK), because of their potential reactivity with the reactants, intermediates and/or benzoxazine product, are not suited for the practice of the present invention.

Like ether solvents, alkyl halide solvents (such as methylene chloride, chloroform, and carbon tetrachloride) because of their toxicity, are not suited for the practice of the present invention.

The boiling point of ethyl acetate is more than 20° C. lower than that of toluene under a vacuum of slightly less than 0.1 MPa. The benzoxazine can therefore be dried at 70° C., without the risk of advancing the product and thus increasing its viscosity (leading to a compromised shelf life stability). The benzoxazine product made in ethyl acetate is solvent-free indicated by gas chromatography/mass spectrometry (not shown; contrasted with FIG. 1) and shows shelf life stability at 120° C. by a rheometric viscosity measurement compared to the benzoxazine made in toluene (see FIG. 2, A and B).

BRIEF DESCRIPTION OF THE FIGURES

FIG. 2 depicts in two parts a gel permeation chromatogram of a benzoxazine prepared in toluene (A) compared with benzoxazine prepared in ethyl acetate (B).

DETAILED DESCRIPTION OF THE INVENTION

Figure 1:
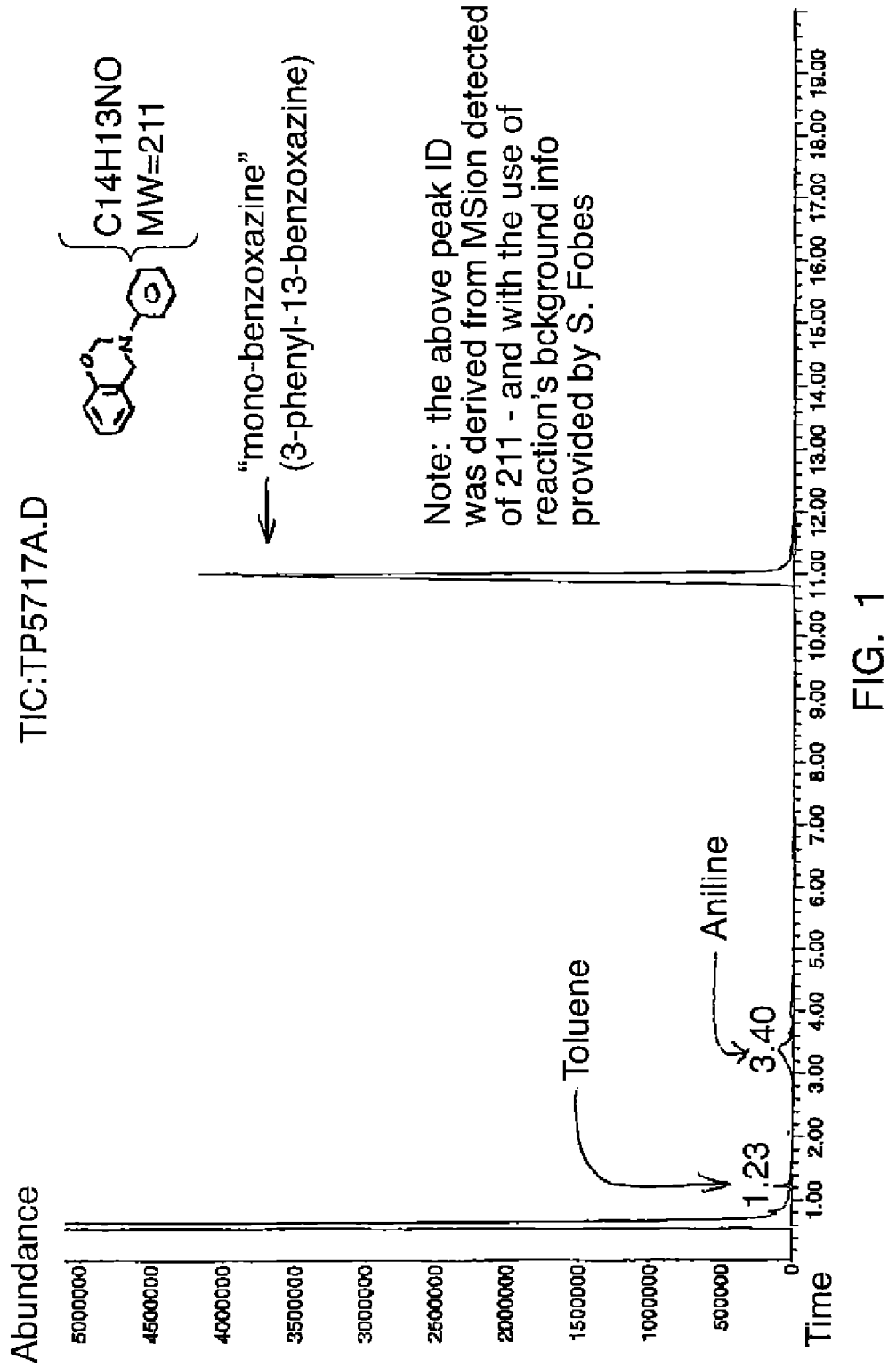
FIG. 1 depicts a gas chromatography/mass spectrometry trace of a benzoxazine prepared in toluene.

As previously indicated, until now, benzoxazine resins have been synthesized from a phenol, an aldehyde, and a primary amine in solvents such as toluene, dioxane, and alcohol, or in a solventless system. Typically, the reaction to complete the synthesis of the benzoxazine compound takes more than several hours, due to the time necessary for the synthesis and subsequent solvent removal. Additional time is necessary if purification of the product is desired. While the yield of benzoxazine and molecular weight distribution using techniques employing a solvent are satisfactory, it is desirable to choose alternative solvents because of toxicity, high boiling points, miscibility with water and reactivity with reactants, intermediates and/or benzoxazine product.

While no catalyst is required for the reaction leading to the products previously described, if desired, for instance in order to change the composition of the products formed in the reaction mixture, acid catalysts such as HCl, or basic catalysts, for instance, NaOH, may be employed.

Any of various aldehydes may be employed for the synthesis, for example, formaldehyde in solution (e.g., formalin), paraformaldehyde, polyoxymethylene, as well as aldehydes having the general formula RCHO, where R is aliphatic, including mixtures of such aldehydes.

A host of phenols may likewise be used in the synthesis. One may use, for example, mono-functional phenols such as phenol, cresol, 2-bromo-4-methylphenol, 2-allyphenol, 1,4-aminophenol, or the like. Suitable di-functional phenols include phenolphthalein, biphenol, 4-4'-methylene-di-phenol, 4-4'-dihydroxybenzophenone, bisphenol-A, 1,8-dihydroxyanthraquinone, 1,6-dihydroxnaphthalene, 2,2'-dihydroxyazobenzene, resorcinol, fluorene bisphenol, and the like. Suitable tri-functional phenols include 1,3,5-trihydroxy benzene and the like.

Many primary amines may be used in the synthesis of benzoxazine. Suitable compounds include monofunctional amines such as ammonium, methylamine, ethylamine, propylamine, butylamine, isopropylamine, octadecylamine, cyclohexylamine, alkylamine, 1-aminoanthracene, 4-aminobenzaldehyde, 4-aminobenzophenone, aminobiphenyl, 2-amino-5-bromopyridine, D-3-amino-e-caprolactam, 2-amino-2,6-dimethylpiperidine, 3-amino-9-ethylcarbazole, 4-(2-aminoethyl)morpholine, 2-aminofluorenone, 2-aminofluorene, 1-aminohomopiperidine, 9-aminophenanthrene, 1-aminopyrene, 4-bromoaniline, aniline, and the like. Suitable di-functional amines include 2-amino-benxylamine, 1,3-diaminopropane, 1,4-diaminobutane, 1,10-diaminodecane, 2,7-diaminofluorene, 1,4-diaminocyclohexane, 9,10-diaminophenanthrene, 1,4-diaminopiperazine, methylenedianiline, 1,4-diaminobenzophenone, 4,4'-diaminodiphenylsulfone, fluorenediamine, 4,4'-diaminodiphenylsulfide, 4,4'-oxydianiline, and the like. Suitable tri-functional amines include melamine, while tetrafunctional amines include fluorenetetraamine, tetraaminediphenylether, and the like.

In addition, amine-functionalized polydimethylsiloxane and copolymers thereof, amine-functionalized polybutadiene and its copolymers, polyallylamine, and the like.

With respect to reaction conditions, the reaction can proceed at approximately room temperature given sufficient time, or the reaction temperature may be controlled to about 150° C.

The reaction synthesis may be conducted at atmospheric pressure or at a pressure up to about 100 psi, if desired.

The time of reaction will depend upon the nature of the reactants, as well as the reaction conditions. Commonly, however, a reaction time of about 15 to about 30 minutes is employed, although as stated, the reaction time may be either less or greater than that period, depending upon the circumstances of the reaction.

The relative amounts of the reactants required will depend upon their chemical nature, e.g., the number of reactive groups taking part in the reaction. The stoichiometry is well within the skills of those conversant with the art, and the required relative amounts of reactants are readily selected, depending upon the functionality of the reacting compounds.

The benzoxazine may be embraced by the following structure:

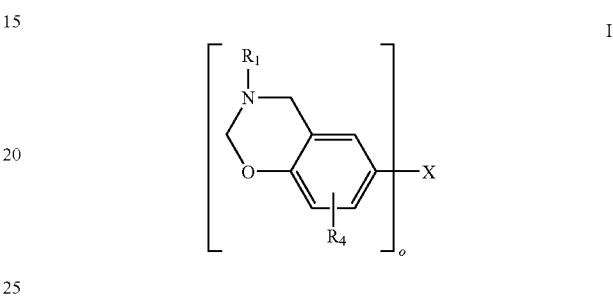

I where o is 1-4, X is selected from a direct bond (when o is 2), alkyl (when o is 1), alkylene (when o is 2-4), carbonyl (when o is 2), thiol (when o is 1), thioether (when o is 2), sulfoxide (when o is 2), and sulfone (when o is 2), $R_1$ is selected from hydrogen, alkyl, alkenyl and aryl, and $R_4$ is selected from hydrogen, halogen, alkyl and alkenyl.

More specifically, within structure I the benzoxazine may be embraced by the following structure:

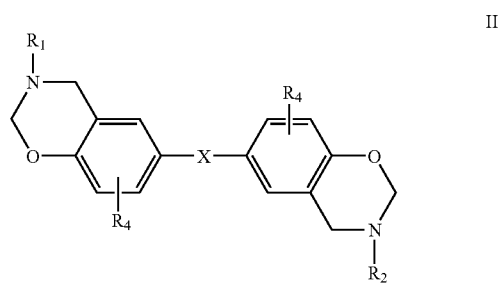

II where X is selected from a direct bond, $CH_2$, $C(CH_3)_2$, $C=O$, S, $S=O$ and $O=S=O$, $R_1$ and $R_2$ are the same or different and are selected from hydrogen, alkyl, such as methyl, ethyl, propyls and butyls, alkenyl, such as allyl, and aryl and $R_4$ are the same or different and are selected from hydrogen or alkenyl, such as allyl.

Representative benzoxazines within structure II include:

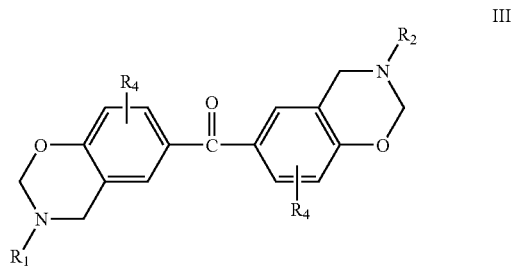

III

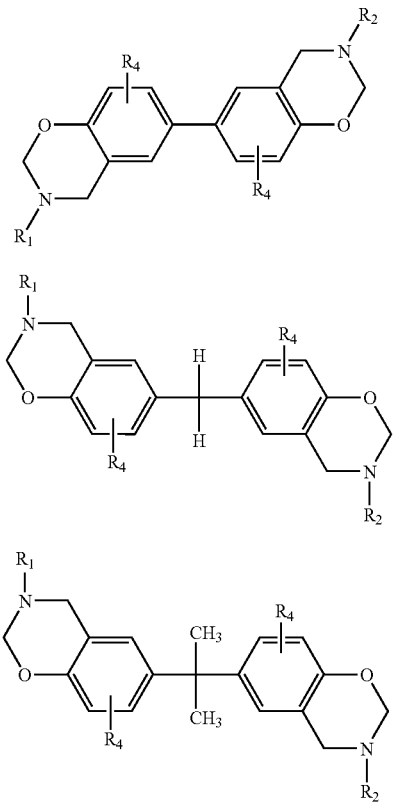

where $R_1$, $R_2$ and $R_4$ are as defined above.

Alternatively, the benzoxazine may be embraced by the following structure:

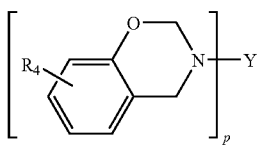

where p is 2, Y is selected from biphenyl (when p is 2), diphenyl methane (when p is 2), diphenyl isopropane (when p is 2), diphenyl sulfide (when p is 2), diphenyl sulfoxide (when p is 2), diphenyl sulfone (when p is 2), and diphenyl ketone (when p is 2), and $R_4$ is selected from hydrogen, halogen, alkyl and alkenyl.

Though not embraced by structures I or VII additional benzoxazines are within the following structures:

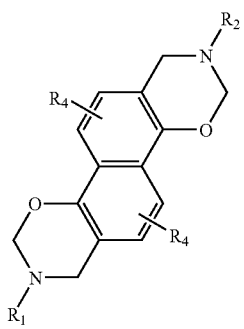

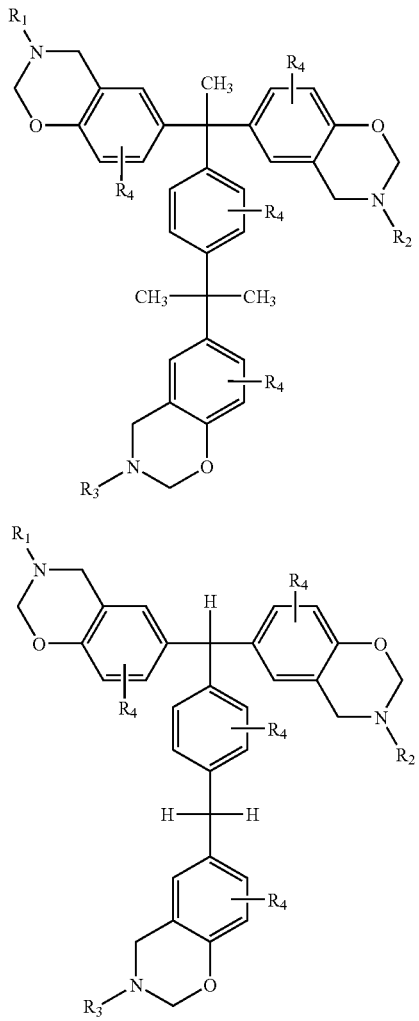

where $R_1$, $R_2$ and $R_4$ are as defined above, and $R_3$ is defined as $R_1$, $R_2$ or $R_4$.

Specific examples of these benzoxazines include:

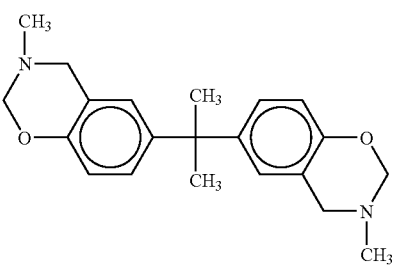

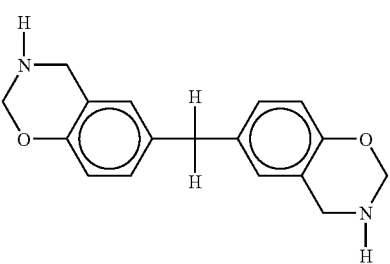

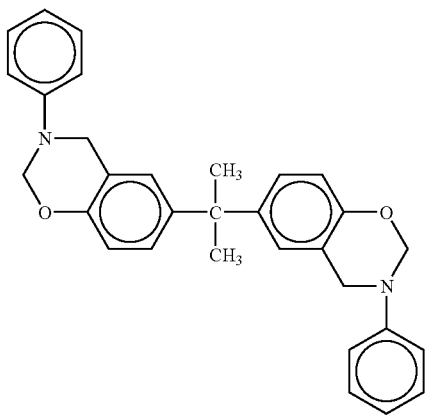

XIII

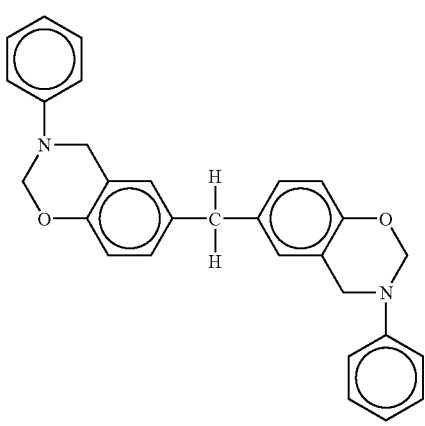

XIV

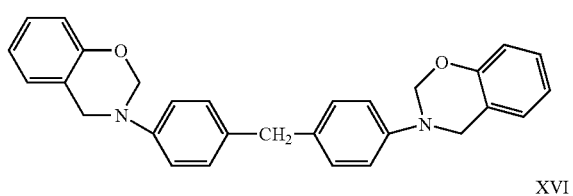

XV

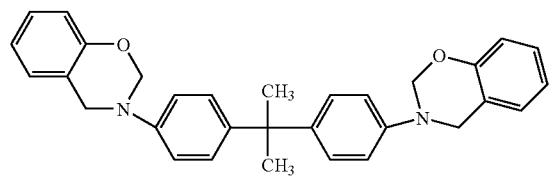

XVI

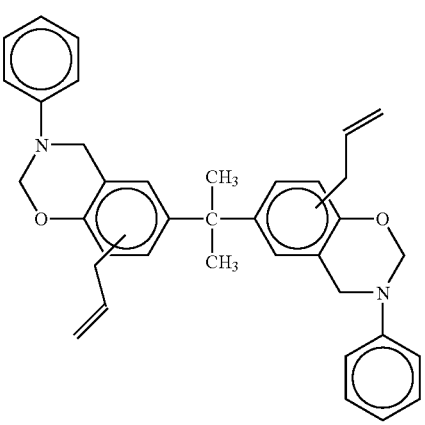

XVII

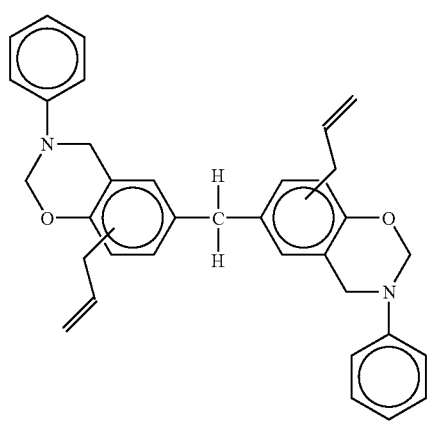

XVIII

The benzoxazine component may include the combination of multifunctional benzoxazines and monofunctional benzoxazines, or may be the combination of one or more multifunctional benzoxazines or one or more monofunctional benzoxazines.

Examples of monofunctional benzoxazines may be embraced by the following structure:

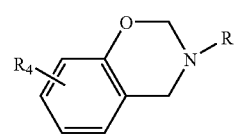

XIX where R is alkyl, such as methyl, ethyl, propyls and butyls, or aryl with or without substitution on one, some or all of the available substitutable sites, and $R_4$ is selected from hydrogen, halogen, alkyl and alkenyl.

For instance, monofunctional benzoxazines may be embraced by the structure

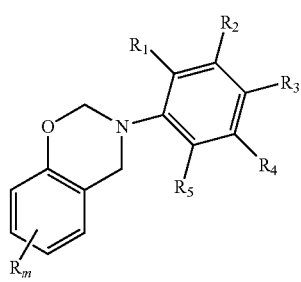

XX where in this case R is selected from alkyl, alkenyl, each of which being optionally substituted or interrupted by one or more O, N, S, C=O, COO, and NHC=O, and aryl; m is 0-4; and $R_1$-$R_5$ are independently selected from hydrogen, alkyl, alkenyl, each of which being optionally substituted or interrupted by one or more O, N, S, C=O, COOH, and NHC=O, and aryl.

Specific examples of such a monofunctional benzoxazine are:

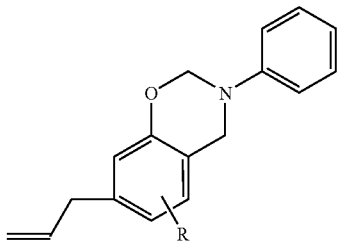

XXI where R is as defined above; or

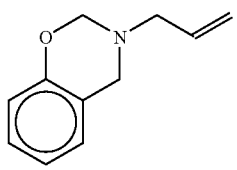

The examples below help illustrate the present invention.

EXAMPLES

Two reactions were conducted, one in toluene and the other in ethyl acetate. In the first reaction, 135 g of a 37% solution of formalin was added to 70.5 g of phenol and 27.9 g of aniline, together with 44.6 g of methylene diamine. Toluene in an amount of 69 q was used as a solvent. The reaction mixture was allowed to stir at room temperature and heated to a temperature of 80° C. The mixture was allowed to continue to react for a period of time of five hours at a reflux temperature of about 80° C.

In the second reaction, the same amounts of reactants were combined, though the amount of the ethyl acetate used in this case is 71.95 g instead of 69 g of toluene. Here, the reaction mixture was allowed to stir at room temperature, and then heated to a reflux temperature, beginning at about 65° C., and settling at 78° C. or less. The mixture was then allowed to continue to react for a period of time of five hours at a reflux temperature.

When each reaction was complete, three aqueous sodium hydroxide washes were made, followed by two water washes. The washed reaction mixture was then dried and concentrated under a reduced pressure and a temperature of 80° C. to 93° C. in the case of the first reaction and up to 70° C. in the case of the second reaction.

Reference to FIG. 2 shows for each benzoxazine product of the two reactions major peaks are at 317 for difunctional benzoxazine monomer and 102 for monofunctional benzoxazine monomer. The other peaks are impurities: raw materials, intermediates, or oligomers. Qualitatively, the benzoxazine products from the two reactions are the same, though reference to FIG. 2, A shows a higher amount of material between 15.5-18 minutes is observed. This material—a high molecular weight oligomeric material—correlates with the higher temperatures used during the drying process needed to remove the toluene. These high molecular weight oligomeric materials are believed to cause some of the instability in the final benzoxazine product made from a toluene solvent.

Figure 3:
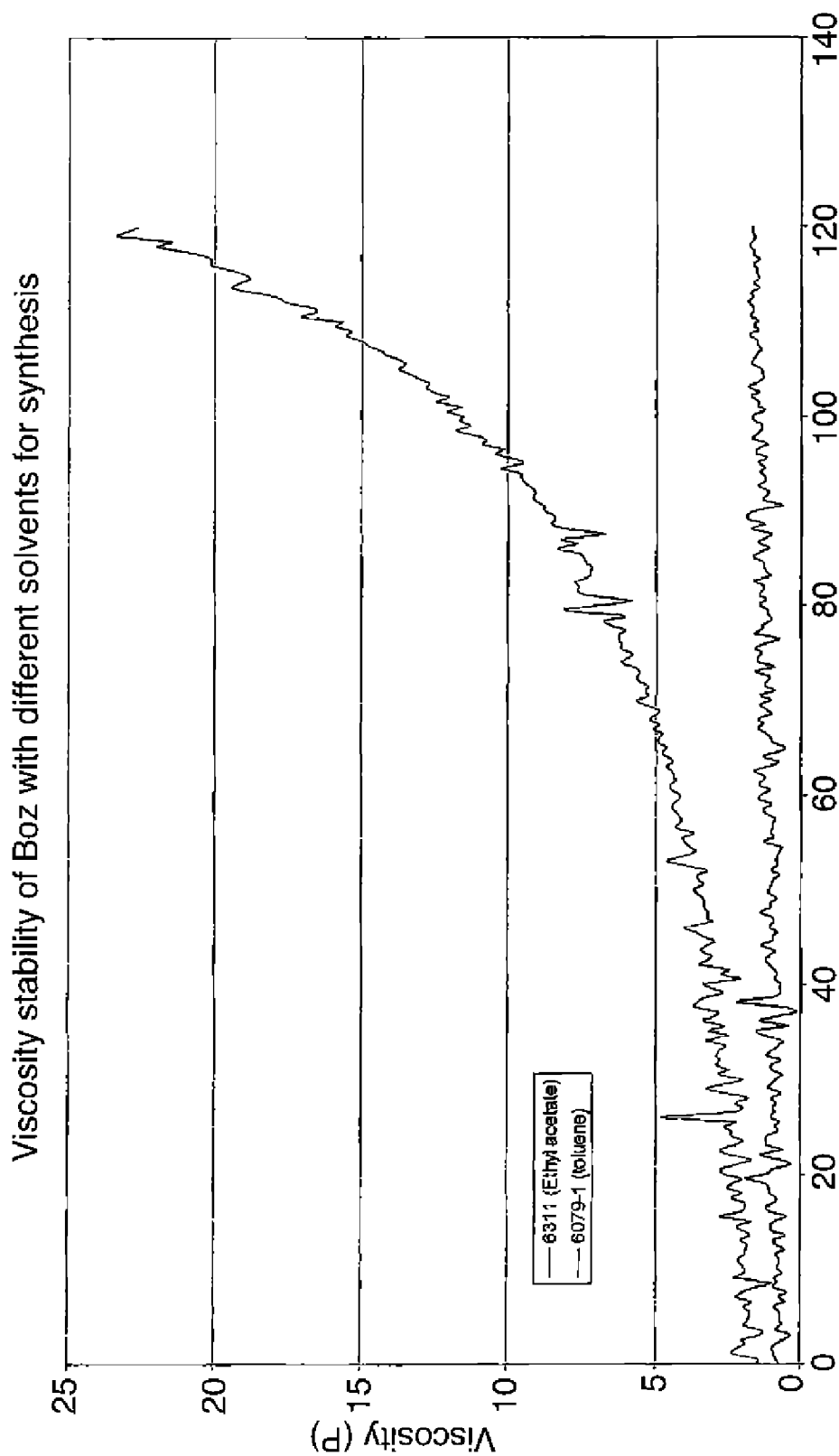
FIG. 3 depicts a trace of a rheometric viscosity measurement over time of a benzoxazine prepared in toluene (the upper curve) compared with benzoxazine prepared in ethyl acetate (the lower curve).

Reference to FIG. 3 shows rheometric viscosity measurements at 120° C. over time of a benzoxazine prepared in toluene (the upper curve) compared with benzoxazine prepared in ethyl acetate (the lower curve). The relative flatness of the lower curve indicates stability in terms of viscosity build up (which translates into an advancement of the benzoxazine product caused by reaction), whereas the increase in the upper curve shows the opposite result.

The advancement of the benzoxazine product caused by reaction at 120° C. over time as indicated in the preceding paragraph and with reference to FIG. 3 may be explained by benzoxazine ring opening caused by extensive heat-aging at a temperature of up to 93° C. during the drying of the product to remove toluene.

What is claimed is:

1. A method for preparing a 1,3-benzoxazine comprising:
   (a) preparing a reaction mixture containing as reactants (i) a phenolic component; (ii) a primary amine component; and (iii) an aldehyde component in an alkyl acetate solvent; and
   (b) bringing the reactants and solvent to a temperature at which the reactants combine chemically and maintaining them at that temperature for a time sufficient to form the benzoxazine.

2. The method of claim 1, wherein the alkyl ester solvent is selected from the group consisting of ethyl acetate, propyl acetate, isopropyl acetate and propyl formate.

3. The method of claim 1, further comprising washing the reaction mixture of step (b) with aqueous alkali.

4. The method of claim 1 further comprising washing the reaction mixture of step (b) with water.

5. The method of claim 1, wherein the benzoxazine is formed in a yield of about 90% or better.

6. The method of claim 1 wherein the temperature in step (b) is about 65° C. or more.

7. The method of claim 1, wherein the reaction occurs within a period of time of 5 hours.

8. The method of claim 1, wherein the solvent is removed at an elevated temperature.

9. The method of claim 8, wherein the temperature is about 70° C.

10. The method of claim 1, wherein the benzoxazine may be embraced by one or more of the following structures:

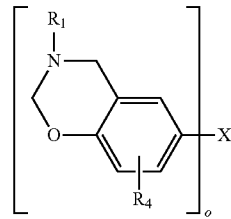

wherein o is 1-4, X is selected from direct bond (when o is 2), alkyl (when o is 1), alkylene (when o is 2-4), carbonyl (when o is 2), thiol (when o is 1), thioether (when o is 2), sulfoxide,(when o is 2), and sulfone (when o is 2), $R_1$ is selected from hydrogen, alkyl, alkenyl and aryl, and $R_4$ is selected from hydrogen, halogen, alkyl and alkenyl; or

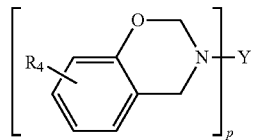

wherein p is 2, Y is selected from biphenyl (when p is 2), diphenyl methane (when p is 2), diphenyl isopropane (when p is 2), diphenyl sulfide (when p is 2), diphenyl sulfoxide (when p is 2), diphenyl sulfone (when p is 2), and diphenyl ketone (when p is 2), and $R_4$ is selected from hydrogen, halogen, alkyl and alkenyl.

11. The method of claim 1, wherein the time is between about 0.5 to about 30 minutes.

* * * * *